United States Patent
Pane et al.

(10) Patent No.: US 11,458,176 B2
(45) Date of Patent: *Oct. 4, 2022

(54) COMPOSITION FOR USE IN THE TREATMENT AND/OR IMPROVEMENT OF SLEEP AND MOOD DISORDERS

(71) Applicant: PROBIOTICAL S.P.A., Novara (IT)

(72) Inventors: Marco Pane, Novara (IT); Angela Amoruso, Novara (IT); Mirta Fiorio, Novara (IT); Angela Marotta, Novara (IT); Giovanna Felis, Novara (IT); Antonio Del Casale, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/769,526

(22) PCT Filed: Dec. 19, 2018

(86) PCT No.: PCT/IB2018/060362
§ 371 (c)(1),
(2) Date: Jun. 3, 2020

(87) PCT Pub. No.: WO2019/123328
PCT Pub. Date: Jun. 27, 2019

(65) Prior Publication Data
US 2020/0390832 A1    Dec. 17, 2020

(30) Foreign Application Priority Data
Dec. 19, 2017  (IT) .................. 102017000146791

(51) Int. Cl.
*A61K 35/747* (2015.01)
*A61P 25/00* (2006.01)
*A61K 9/00* (2006.01)
*A61K 9/08* (2006.01)
*A61K 35/745* (2015.01)

(52) U.S. Cl.
CPC .......... *A61K 35/747* (2013.01); *A61K 9/0053* (2013.01); *A61K 9/08* (2013.01); *A61K 35/745* (2013.01); *A61P 25/00* (2018.01)

(58) Field of Classification Search
None
See application file for complete search history.

(56) References Cited

U.S. PATENT DOCUMENTS

2017/0326186 A1   11/2017  Mogna

FOREIGN PATENT DOCUMENTS

| WO | WO 2014/184643 A1 | 11/2014 | |
|----|-------------------|---------|--|
| WO | WO-2016084029 A1 * | 6/2016 | ............. A61K 35/74 |
| WO | WO 2018/029629 A1 | 2/2018 | |

OTHER PUBLICATIONS

Logan et al., "Major depressive disorder: probiotics may be an adjuvant therapy", Medical Hypotheses, 2005, 64: 533-538.
Anonymous: "Mood Probiotic by InnovixLabs", Jan. 1, 2016, retrieved from the Internet: URL:https://www.amazon.com/PROBIOTIC-InnovixLabs-probiotic-clinically-Capsules/dp/B00ZMO7UKW/ref=sr_1_3_s_it?s=hpc&ie=UTF8&qid=1536131865&sr=1-3&keywords=Mood+Probiotic [retrieved on Sep. 5, 2018].
Anonymous: "Mood+ by Garden of Life", Jan. 1, 2015, retrieved from the Internet: URL:https://www.amazon.com/Garden-Life-Probiotic-Mood-Supplement/dp/B01LVYJK6U [retrieved on Sep. 6, 2018].
Zhou et al., "Psychobiotics and the gut-brain axis: in the pursuit of happiness", Neuropsychiatric Disease and Treatment, 2015, 11: 715-723.

* cited by examiner

*Primary Examiner* — Brian Gangle
(74) *Attorney, Agent, or Firm* — James S. Keddie; Bozicevic, Field & Francis LLP

(57) ABSTRACT

The present invention refers to a composition for use in the treatment of sleep disorder, in particular, in the improvement of sleep quality. Furthermore, the present invention refers to a composition for use in the treatment of mood modulation.

3 Claims, 9 Drawing Sheets

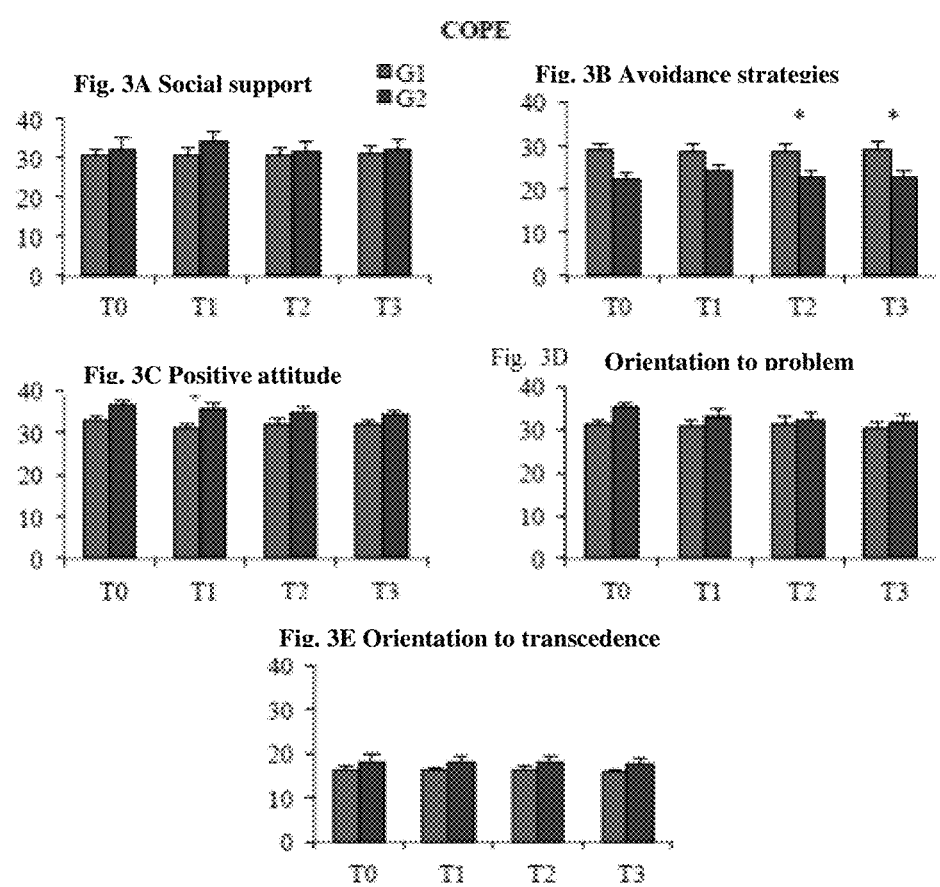

Figure 1:
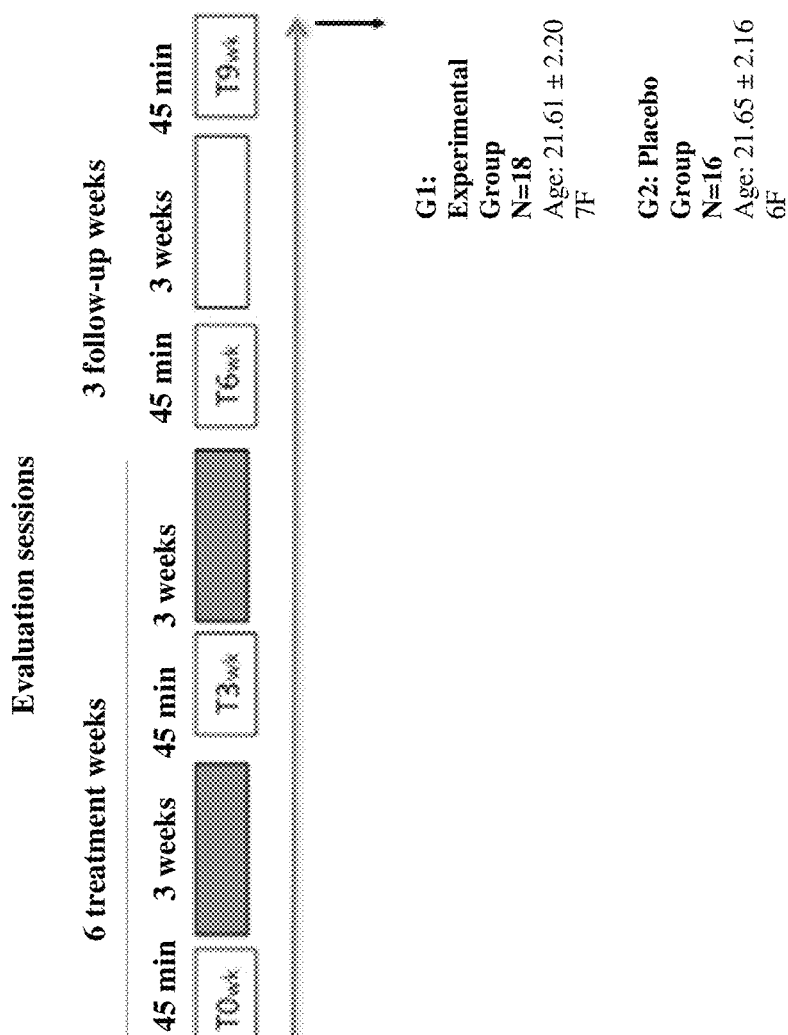

LEIDS
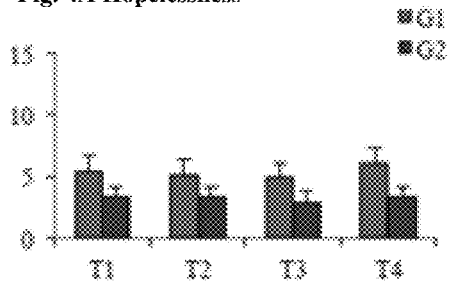
Fig. 4A Hopelessness
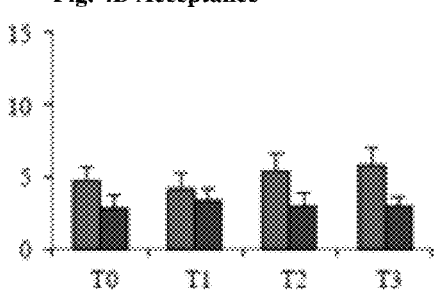
Fig. 4B Acceptance
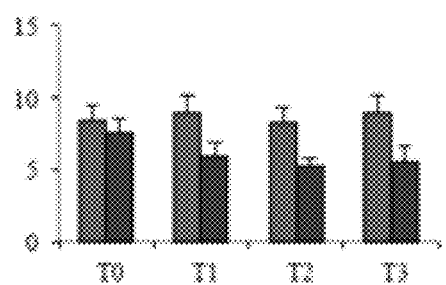
Fig. 4C Aggressiveness
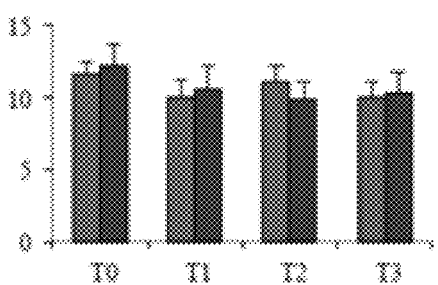
Fig. 4D Rumination
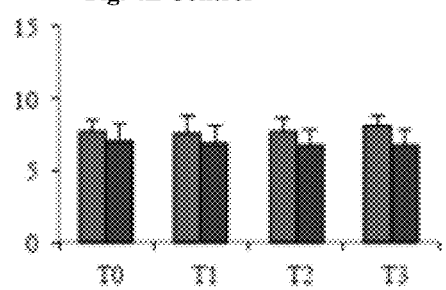
Fig. 4E Control
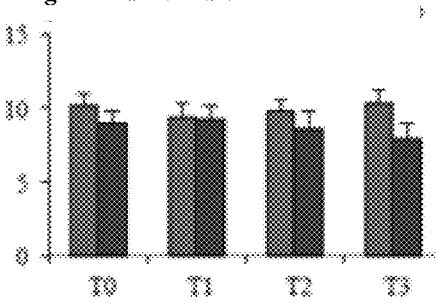
Fig. 4F Risk aversion

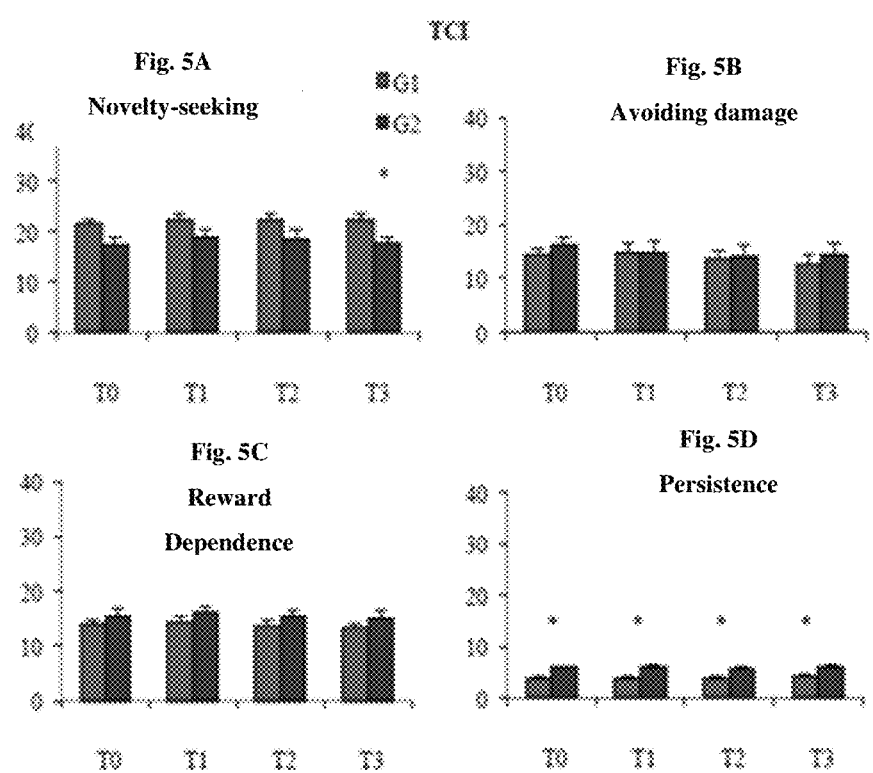

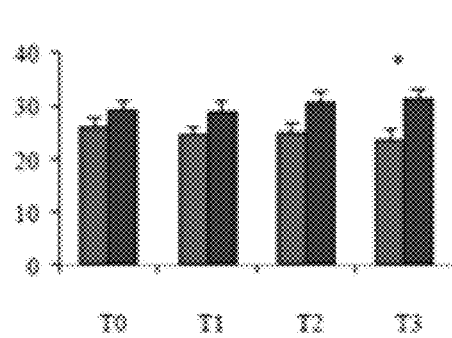
Fig. 5E Self-direction
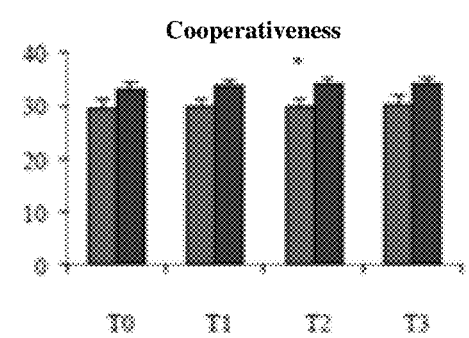
Fig. 5F Cooperativeness
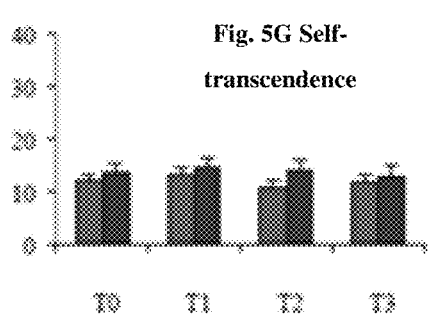
Fig. 5G Self-transcendence

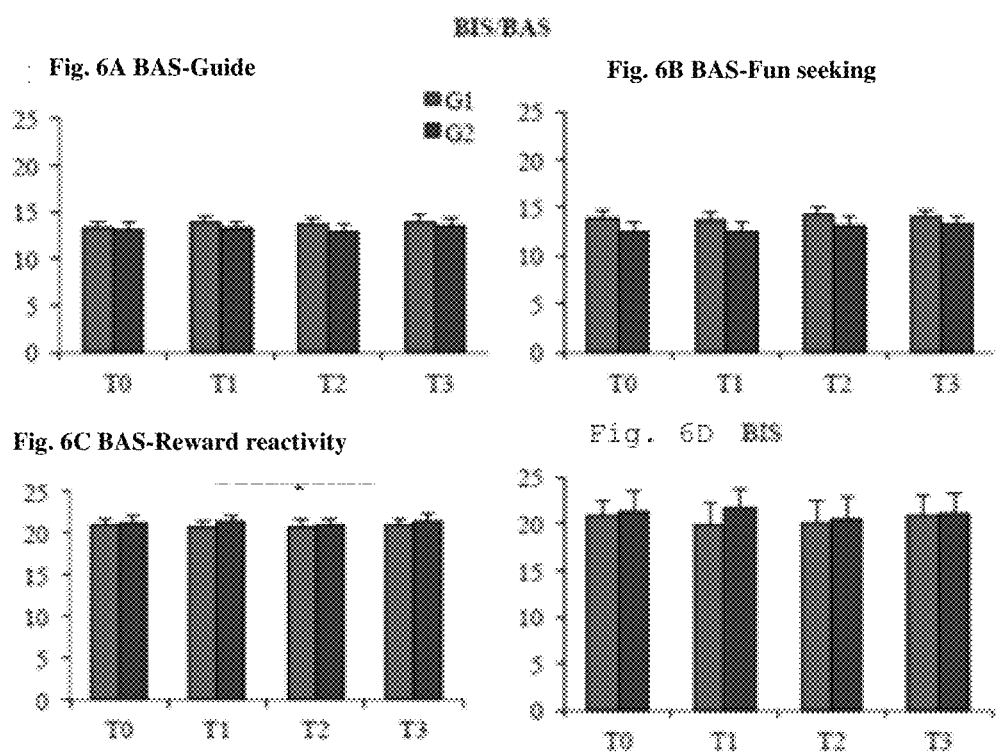

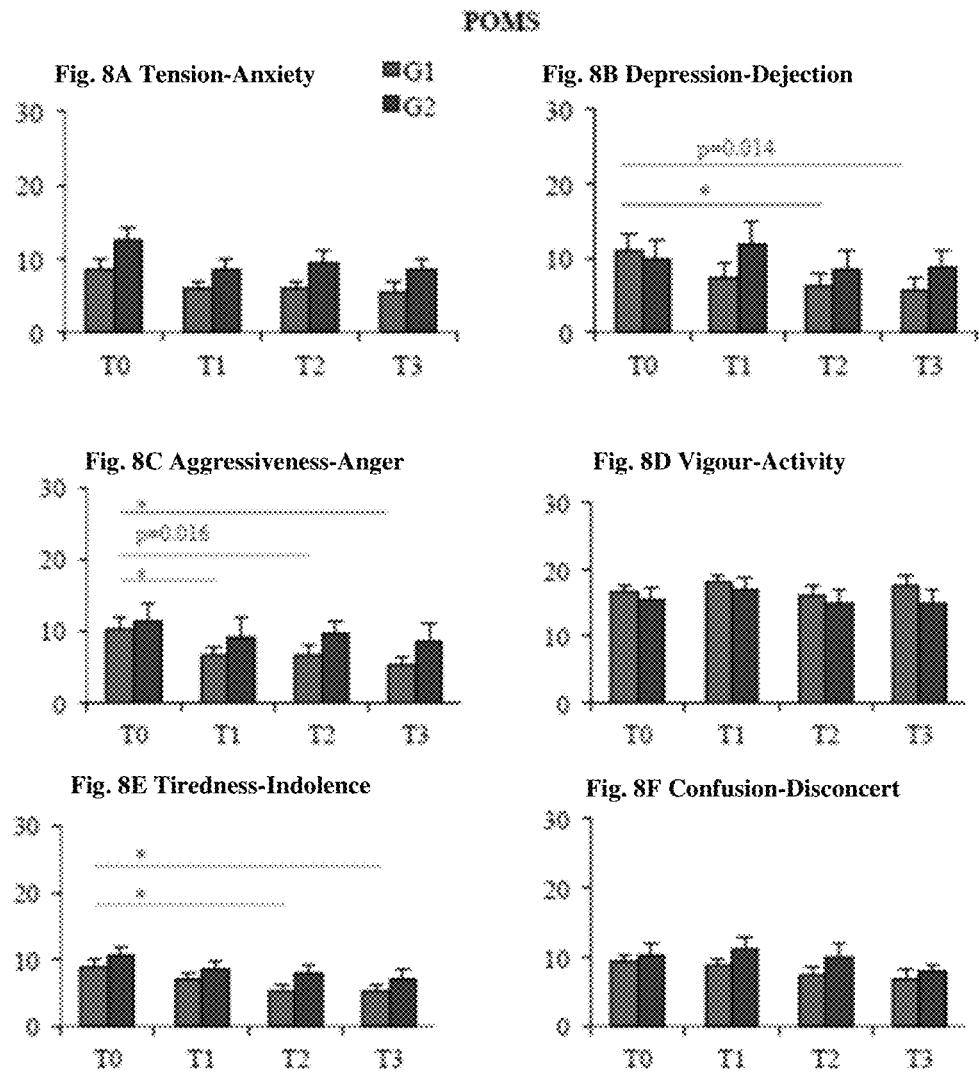

COMPOSITION FOR USE IN THE TREATMENT AND/OR IMPROVEMENT OF SLEEP AND MOOD DISORDERS

CROSS-REFERENCE TO RELATED APPLICATIONS

This application is a § 371 national phase of International Application No. PCT/IB2018/060362, filed on Dec. 19, 2018, which claims the benefit of Italian Application No. 102017000146791, filed on Dec. 19, 2017, which applications are incorporated by reference herein.

The present invention refers to a composition comprising a bacteria strains mixture for use in a method for the treatment and/or improvement of a sleep disorder, in particular in the treatment and/or improvement of a sleep quality disorder and/or insomnia.

Furthermore, the present invention refers to said composition comprising said bacteria strains mixture for use in a method for treating mood modulation.

Sleep is defined as a state of sleep as opposed to wakefulness, condition of physical and mental rest characterised by the temporary detachment of consciousness and willingness, the slowing down of neurovegetative functions and the partial interruption of the sensorimotor relationships of the subject with the environment, indispensable for the rest of the organism. An appropriate sleep is biological necessary to support life. The physical and mental health condition of the person depends on the quality and duration of sleep.

The International classification of sleep disorders (ICSD 2005) gathers more than 90 of them. The most common sleep diseases can be distinguished into dyssomnias, parasomnias and breathing-related sleep disorders, which are part of the primary group of sleep disorders.

Dyssomnias are disorders that prevent the person from falling asleep or cause them to wake up prematurely and they are characterised by dysfunctional sleep quality, quantity and time. Particularly known among dyssomnias is insomnia, characterised by failure to fall asleep. Insomnia is associated to poor daytime functioning, with symptoms such as tiredness, irritability, learning difficulty, lack of memory consolidation and marked loss of interest to carry out daily chores. Extended insomnia for more than a few nights in a row can become "chronic" and cause a sleep deficit which is extremely harmful for the health of the insomniac.

Parasomnias usually occur in the non-REM sleep stage and they are mainly related to psychological sleep and dream disorders.

Sleep disorders may affect the physical and mental health of the person suffering from them jeopardising the quality of life thereof.

In psychiatry and psychology, the term mood disorder or mood dysregulation is used to indicate the vast class of psychopathological disorders and symptoms consisting in alterations or abnormalities of the mood state of the person, of magnitude such to cause persistent or reiterated problems of dysfunctions or marked discomfort to the person as well as maladjustment to the environmental conditions of life. A mood dysregulation may affect the physical and mental health condition of the person suffering from it jeopardising the quality of life thereof.

Mood disorders and sleep disorders are closely correlated given that often one leads to the other and vice versa. As a matter of fact, altered mood tones can cause sleep disorders, in particular they can affect the sleep quality of the person or cause insomnia. Vice versa, sleep disorders, in particular if extended over time, lead to a wakefulness-sleep ratio imbalance of the person thus leading to a more or less serious alteration of the mood state thereof.

Though there is no unique solution for sleep disorders, there is a wide range of possible solutions, some of which arising from popular traditions and others as a result of pharmaceutical research. A healthy lifestyle, psychological treatments and meditations, herbal remedies and melatonin are some of the most widely known "people's" remedies. Barbiturates, benzodiazepines, neuroleptics, non-benzodiazepine hypnotics, and pyrazolopyrimidines instead are categories of psychiatric medications administered to treat sleep disorders.

Scientific research has shown that sleep disorder treatments, in particular both for sleep quality disorders and insomnia proposed up to date reveal drawbacks, such as:
i) poor effectiveness;
ii) immunological tolerance over time, assuefaction (i.e. loss of response towards the drug by the body) like in the case of benzodiazepines and non-benzodiazepine hypnotics;
iii) addiction, like in the case of benzodiazepines and non-benzodiazepine hypnotics; and
iv) adverse effects, ranging from mild to serious like in the case barbiturates (e.g. poisoning, cardiorespiratory depression).

Similarly, even as regards mood dysregulation disorders there currently exists a wide range of potential remedies, deriving from pharmaceutical and non-pharmaceutical research, such as: psychological treatments, pharmacological antidepressants which act on monoaminergic systems, lithium salts, low-dose antiepileptics, neuroleptics (antipsychotics), anxiolytics (e.g. benzodiazepines) or psychostimulants, and nonsteroidal anti-inflammatory drugs.

Even in this case, scientific research proved that treatments aimed at facilitating mood modulation proposed up to date reveal drawbacks, such as:
i) poor effectiveness and full absence of response to treatment;
ii) adverse effects ranging from mild to serious.

Thus, interest by operators of the industry towards finding an effective solution for treating subjects, both healthy and pathological, affected a) by sleep disorders, in particular by sleep quality disorders and/or insomnia and/or b) by mood disorder or mood dysregulation, in particular mood instability over time, that offers a valid and alternative solution to current natural and pharmacological treatments, in particular with specific reference to an increase of the percentage of subjects in whom the treatment is effective, to absence of assuefaction to the treatment over time and to a reduction of the adverse effects remains high.

In particular, there arises the need to be able to provide products, compositions, formulations, medical devices, food supplements or foodstuffs capable of reducing and/or mitigating symptoms arising from or related a) to sleep disorders, in particular sleep quality disorders and/or insomnia, and/or b) to mood disorder or mood dysregulation, in particular mood instability of time among healthy and pathological subjects, so as to allow an improvement of the quality of life and an improvement or a maintenance of the physical and mental condition of the subjects affected by such disorders, an increase of the percentage of subjects in whom the treatment is effective and a reduction of the adverse effects.

An object of the present invention is to provide an appropriate response to the limits still observable in products of the prior art and to the technical problem described above.

SUMMARY OF THE INVENTION

The Applicant found it useful to study and deepen the therapeutic potential of the gut microbiota in the treatment of sleep disorders, in particular sleep quality disorders or insomnia, and mood dysregulation disorders.

The interaction between the immune system and the brain as concerns sleep disorders and mood disorders has mainly focused on the evaluation of structural modifications, through metagenomic analysis, in terms of composition of the gut ecosystem in favour of selecting groups of microorganisms involved in the exchange of positive signals through the gut-brain communication axis.

Following an intense and extended research and development activity, the Applicant developed a treatment therapy based on a composition comprising at least one bacterial strain or a bacteria strains mixture to be administered a) to subjects suffering from a sleep disorder, in particular a sleep quality disorder or insomnia and/or b) to subjects suffering from a mood disorder or mood dysregulation, in particular suffering from a mod instability extended over time, capable of overcoming the limits and drawbacks present in the prior art and providing an effective solution to the technical problem described above.

In addition, the Applicant developed the use, not for therapeutic purposes, of said composition comprising said bacteria strains mixture a) for modulating and/or improving sleep disorders, preferably sleep quality disorders or insomnia (insomnia not intended as a disease), and/or b) for facilitating mood modulation, capable of overcoming the limits and drawbacks present in the prior art and providing an effective solution to the technical problem described above.

A composition comprising at least one bacterial strain or a bacterial strains mixture and, optionally technological additives and/or pharmaceutical or food grade excipients, for use in a method for treating sleep disorders, in particular a sleep quality disorder and/or insomnia, and/or mood disorders or mood dysregulation, in particular mood instability extended over time, having the characteristics as outlined in the attached independent claims, forms an object of the present invention.

The use, not for therapeutic purposes, of said composition comprising said bacteria strains mixture a) for modulating and/or improving sleep disorders, preferably sleep quality disorders and/or insomnia (insomnia not intended as a disease), and/or b) for facilitating mood modulation, having the characteristics as indicated in the attached independent claim forms a further object of the present invention.

Preferred embodiments of the present invention are indicated in the attached dependent claims.

The preferred embodiments of the present invention described in the description that follows, are indicated herein solely by way of non-limiting example of the extensive field of application of the present invention, which will be instantly clear to the man skilled in the art.

FIGURES

FIG. 1 refers to the evaluation sessions (6 weeks of treatment +3 weeks of follow-up).

Figure 2:
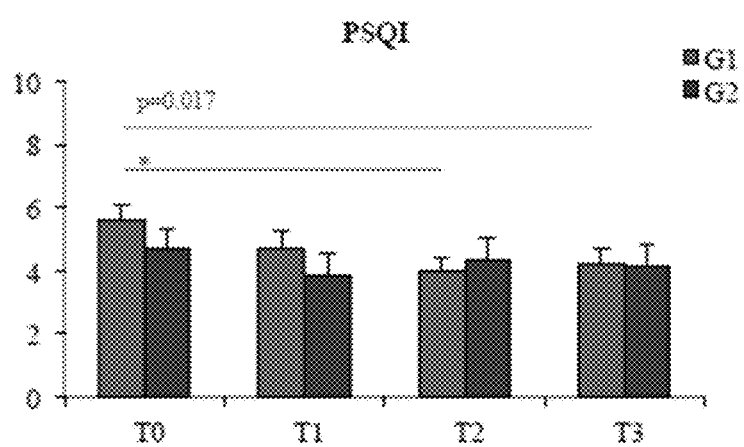

FIG. 2 refers to the evaluation of sleep quality (PSQI Mean Score as a function of time T0, T1, T2 and T3) in the two groups: Experimental group G1 and Control group G2.

FIGS. 3A, 3B, 3C, 3D and 3E refer to the evaluation of the capacity to address stressing events/situations (COPE: Social support, Avoidance strategies, Positive attitude, Orientation to problem, Orientation to transcendence as a function of time T0, T1, T2 and T3) in the two groups: Experimental group G1 and Control group G2.

FIGS. 4A, 4B, 4C, 4D, 4E and 4F refer to the evaluation of the cognitive relativity (LEIDS-R: Hopelessness, Acceptance, Aggressiveness, Rumination, Control and Risk aversion as a function of time T0, T1, T2 and T3) in the two groups: Experimental group G1 and Control group G2.

FIGS. 5A, 5B, 5C, 5D, 5E, 5F and 5G refer to the evaluation of personality (TCI: Novelty seeking, Avoiding damage, Reward dependence, Persistence, Self-direction, Cooperativeness, Self-transcendence as a function of time T0, T1, T2 and T3) in the two groups: Experimental group G1 and Control group G2.

FIGS. 6A, 6B, 6C and 6D, refer to the evaluation of the dispositional sensitivity towards the behavioural inhibition system (BIS) and towards the behavioural approach or activation system (BAS) (BIS-BAS: BAS-Guide, BAS-Seeking fun, BAS-Reward Reactivity and BIS as a function of time T0, T1, T2 and T3 in the two groups: Experimental group G1 and Control group G2.

Figure 7:
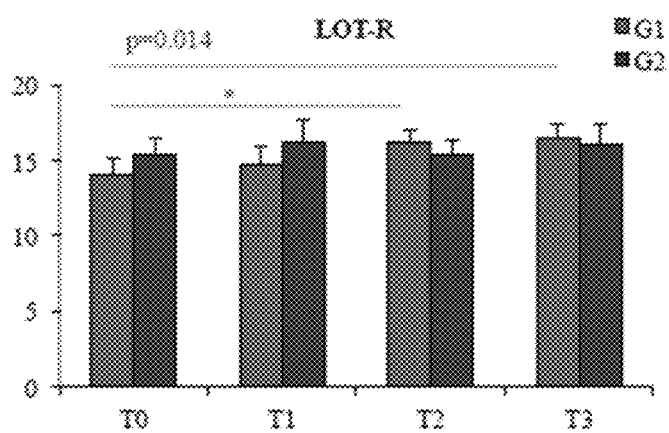

FIG. 7 refers to the evaluation of predisposition towards pessimism and optimism (LOT-R Mean Score as a function of time T0, T1, T2 and T3) in the two groups: Experimental group G1 and Control group G2.

FIGS. 8A, 8B, 8C, 8D, 8E and 8F refer to the evaluation of the general emotional state (POMS: Tension-Anxiety, Depression-Dejection, Aggressiveness-Anger, Vigour-Activity, Tiredness-Indolence and Confusion-Disconcert as a function of time T0, T1, T2 and T3) in the two groups: Experimental group G1 and Control group G2.

DEFINITIONS

In the present application, the expression sleep disorder is used to indicate the wide class of disorders such as: dyssomnias such as primary insomnia, primary hypersomnia, narcolepsy, breathing-related sleep disorders (obstructive sleep apnoea syndrome), circadian rhythm sleep disorder and dyssomnias not otherwise specified; parasomnias such as nightmare disorder, night terror disorder, somnambulism disorder and parasomnias not otherwise specified; sleep disorders related to another mental disorder such as insomnia related to another mental disorder and hypersomnia related to another mental disorder; sleep disorders due to a general medical condition, in particular sleep disorders related to diseases such as neurological disorders, neuropathic pain, heart and lung diseases; sleep motor disorders such as the restless legs syndrome and bruxism; and jet-lag syndrome.

In the present application the expression sleep quality disorder, is used to indicate a sub-class of sleep disorders that make the sleep perceived by the subject as a sleep not fully regenerating the physical and mental condition of the subject. Sleep quality disorders are for example primary sleep disorders classified as parasomnias, such as: nightmare disorder, night terror disorder, somnambulism disorder, sleep motor disorders such as the restless legs syndrome (RLS), periodic limb movements (PLM), bruxism, violent behaviour during sleep and R.E.M. stage disorders, in which the person moves the body thereof to follow what he or she is dreaming.

In the present application the expression insomnia is used to indicate a sub-class of sleep disorders characterised by failure to sleep despite the organism's actual physiological need of it. From a symptomatic standpoint, there are three types of insomnia: initial insomnia, i.e. difficulty to fall asleep, intermittent or middle or lacunary insomnia characterised by frequent awakening at night, terminal insomnia, characterised by premature waking with failure to fall asleep. In the context of the present invention, the aforementioned expression "frequent waking at night" also comprises typical disorders found in new-borns (0-12 months) and children 1 to 12 years, preferably between 1 and 6 years, more preferably between 1 and 4 years.

In the present application the expression mood modulation in a subject suffering from mood dysregulation, in particular mood instability over time, is used to indicate the stabilisation of the mood state of the subject over time at a state capable of allowing the person to carry out normal social life, study and work daily chores. In particular, it is used to indicate the stabilisation of the mood state over time at a positive/optimism state.

The mood or mood state concept indicates the in-depth emotional correlation of our mental activity (e.g. general emotional state, state of anxiety, state of sadness, state of paranoia, state of fear, state of shyness and inclination towards optimism). This can be considered as a characteristic of the subject, such as character habit and as part of the persons temperament.

All strains described and/or claimed in the present patent application were filed in accordance with the Budapest Treaty, as follows:

*Streptococcus thermophilus* ST10 deposited by Probiotical SpA at the DSMZ depository authority in Germany, on 19 Sep. 2011, with deposit number DSM 25246;

*Lactobacillus fermentum* LF16 deposited by Probiotical SpA at the DSMZ depository authority in Germany, on 1 Mar. 2013, with deposit number DSM 26956;

*Lactobacillus plantarum* LP01 deposited by Mofin Srl at the BCCM LMG depository authority in Belgium, on 16 Oct. 2001, with deposit number DSM LMG P-21021;

*Lactobacillus plantarum* LP02 deposited by Mofin Srl at the BCCM LMG depository authority in Belgium, on 16 Oct. 2001, with deposit number DSM LMG P-21020;

*Lactobacillus rhamnosus* LR06 deposited by Probiotical SpA at the DSMZ depository authority in Germany, on 14 Nov. 2008, with deposit number DSM 21981;

*Bifidobacterium longum* BL04 deposited by Probiotical SpA at the DSMZ depository authority in Germany, on 12 Jan. 2010, with deposit number DSM 23233.

DETAILED DESCRIPTION OF THE INVENTION

The present invention regards a composition (C), as defined below, for use in a method for curative and/or preventive treatment and/or improvement of sleep disorder symptoms or diseases, preferably insomnia, and/or a sleep quality disorder and/or mood modulation or mood dysregulation disorder, in particular mood instability extended over time.

Furthermore, the present invention regards the use of said composition (C), as defined below, for modulating and/or improving a sleep disorder, preferably insomnia (insomnia intended not as a disease), and/or a sleep quality disorder and/or for facilitating mood modulation in a subject, wherein said use is not for therapeutic purposes.

Advantageously, in the present invention the methods for treating a sleep disorder, preferably insomnia, and/or a sleep quality disorder or, alternatively, mood modulation disorder or mood dysregulation disorder are effective both for healthy subjects and pathological subjects (patients) who have been diagnosed with a disorder.

In an embodiment, the composition (C) of the present invention comprises or, alternatively, consists of:
(a) a bacteria strains mixture (M) as defined below, and, optionally,
(b) at least one technological additive and/or at least one pharmaceutical or food grade excipient.

In an embodiment, the (a) bacteria strains mixture (M) of the present invention comprising or, alternatively, consisting of at least one bacteria strain selected from among the group comprising or, alternatively, consisting of:

(a-i) a bacterium strain of the *Lactobacillus fermentum* species identified as the *Lactobacillus fermentum* LF16 DSM 26956 bacterium strain, (a-ii) a bacterium strain of the *Lactobacillus plantarum* species identified as the *Lactobacillus plantarum* LP01 LMG P-21021 bacterium strain, (a-iii) a bacterium strain of the *Lactobacillus plantarum* species identified as the *Lactobacillus plantarum* LP02 LMG P-21020 bacterium strain, (a-iv) a bacterium strain of the *Lactobacillus rhamnosus* species identified as the *Lactobacillus rhamnosus* LR06 DSM 21981 bacterium strain; and (a-v) a bacterium strain of the *Bifidobacterium longum* species identified as the *Bifidobacterium longum* BL04 DSM 23233 bacterium strain.

Preferably, said bacteria strains mixture (M) comprises or, alternatively consists of strains (a-i) and (a-ii) and/or (a-iii) and (a-iv) and (a-v), as defined above.

In other words, said bacteria strains mixture (M) comprises or, alternatively consists of: (a-i) and (a-ii) and (a-iii) and (a-iv) and (a-v) or, alternatively, (a-i) and (a-ii) and (a-iv) and (a-v) or, alternatively, (a-i) and (a-iii) and (a-iv) and (a-v), as defined above Preferably, said bacteria strains mixture(M) comprises or, alternatively, consists of:

(a-i) the *Lactobacillus fermentum* LF16 DSM 26956 bacterium strain, and (a-ii) the *Lactobacillus plantarum* LP01 LMG P-21021 bacterium strain, and/or (a-iii) the *Lactobacillus plantarum* LP02 LMG P-21020 bacterium strain, and (a-iv) the *Lactobacillus rhamnosus* LR06 DSM 21981 bacterium strain, and (a-v) the *Bifidobacterium longum* BL04 DSM 23233 bacterium strain.

Advantageously, (b) a technological additive or a pharmaceutical or food grade excipient can be selected from among all substances known to the man skilled in the art of the pharmaceutical or food preparation technique such as, by way of non-limiting example, preservatives, thickeners, sweeteners, food colours, natural and artificial flavours, antioxidants, stabilisers, fillers and their mixtures. Preferably, (b) it is maltodextrin.

Preferably, the bacteria strains of the bacterial strains mixture (M) (a-i) and (a-ii) and/or (a-iii) and (a-iv) and (a-v) are at a mutual weight ratio equivalent to 1:1:1:1, or equivalent to 1:1:1:1:1.

Preferably each single bacteria strain being present in the mixture (M) at a concentration comprised between $1\times10^8$ CFU/AFU and $1\times10^{12}$ CFU/AFU, preferably between $1\times10^9$ CFU/AFU and $1\times10^{11}$ CFU/AFU, with respect to the daily intake; preferably each single strain is present at a concentration of $1\times10^9$ CFU/AFU with respect to the daily intake.

Preferably, said composition (C) comprises or, alternatively, consists of:
(a-i) the *Lactobacillus fermentum* LF16 DSM 26956 bacterium strain, at a concentration of $1\times10^9$ CFU/AFU dose (CFU: Colony Forming Unit; AFU: Active Fluorescent Unit), and
(a-ii) the *Lactobacillus plantarum* LP01 bacterium strain, at a concentration of $1\times10^9$ CFU/AFU dose, and/or
(a-iii) the *Lactobacillus plantarum* LP02 bacterium strain, at a concentration of $1\times10^9$ CFU/AFU dose, and
(a-iv) the *Lactobacillus rhamnosus* LR06 bacterium strain, at a concentration of $1\times10^9$ CFU/AFU dose, and
(a-v) the *Bifidobacterium longum* BL04 bacterium strain, at a concentration of $1\times10^9$ CFU/AFU dose, and, optionally,
(b), preferably maltodextrin.

For example, said composition (C) is a composition of 3.0 g (daily intake) wherein each of the 4 or 5 bacteria strains (a-i) and (a-ii) and/or (a-iii) and (a-iv) and (a-v) is present at the amount of 0.4 g at a concentration of $1\times10^9$ CFU/AFU ($4\times0.1$ g=0.4 g of mixture M) and 2.6 g are of (b) maltodextrin.

In an embodiment, the composition (C) of the present invention comprises, besides
(a) the bacteria strains mixture (M) comprising or, alternatively, consisting of at least one bacteria strain selected from among the group comprising or, alternatively, consisting of: (a-i), (a-ii), (a-iii), (a-iv) and (a-v) as defined above and, optionally,
(b), also:
(c) at least one gum-bacterial strain combination group of gum-bacterial strain combinations a first group of gum-bacterial strain combinations, and/or
(d) at least one vitamin selected from among a second group of vitamins, and/or
(e) at least one salt selected from among a third group of organic and/or inorganic salts, and/or
(f) at least one substance selected from among a fourth group of antioxidant substances.

Advantageously, said first group of gum-bacterial strain combinations comprises or, alternatively, consists of:
(c-i) at least one natural vegetable gum such as tara gum and
(c-ii) the *S. thermophilus* ST10 DSM 25246 bacteria strain; preferably the *S. thermophilus* ST10 DSM 25246 bacteria strain is present at a concentration comprised between $1\times10^8$ CFU/AFU and $1\times10^{12}$ CFU/AFU, preferably between $1\times10^9$ CFU/AFU and $1\times10^{11}$ CFU/AFU, with respect to the daily intake.

Tara gum (natural vegetable gum) is present in combination with the *S. thermophilus* ST 10 DSM 25246 bacteria strain (PCT international patent n.° WO 2014/020408 A1, on behalf of Probiotical SpA) to obtain a mucoadhesive jellifying complex comprising, besides said tara gum, a gum of bacterial origin (exopolysaccharides—EPS) produced by the *S. thermophilus* DSM 25246 ST10 bacteria strain in situ in the gastrointestinal tract in presence of said tara gum.

The first effect is a jellifying effect exerted by tara gum which is maximum in the stomach (maximum protection) and minimum in the colon due to degradation and ensuing loss of effectiveness at protecting the inflamed intestinal mucosae.

The second effect is a protection effect exerted by the gum of bacterial origin, in particular from exopolysaccharides (EPS) produced in situ in the gastrointestinal tract by the *S. thermophilus* DSM 25246 ST10 bacteria strain. This second effect is minimum in the stomach and maximum in the colon where the bacteria reach alive and active and at a high concentration, producing EPS in situ. The bacterial gum produced directly by the *S. thermophilus* ST10 DSM 25246 bacteria strain alongside tara gum, are capable of preserving and protecting the intestinal mucosa so as to avoid, reduce or at least oppose the action of the pathogenic bacteria, detrimental to the mucosa.

These effects which are complementary to each other, combined together, guarantee full protection of the stomach (due to tara gum) and of the gastrointestinal tract (due to the gum of bacterial origin) against bacterial infections.

Advantageously, said composition (C) comprises or, alternatively, consists of:
(a) the bacteria strains mixture (M) comprising or, alternatively, consisting of at least one bacteria strain selected from among the group comprising or, alternatively, consisting of: (a-i), (a-ii), (a-iii), (a-iv) and (a-v) as defined above and
(c) at least one gum-bacterial strain combination selected from among the first group of gum-bacterial strain combinations comprising or, alternatively, consisting of: (c-i), preferably tara gum, and (c-ii), as defined above and, optionally,
(b), preferably maltodextrin.

Advantageously, said composition (C) comprises or, alternatively, consists of:
(a-i), at a concentration of $1\times10^9$ CFU/AFU dose, and
(a-ii), at a concentration of $1\times10^9$ CFU/AFU dose, and/or
(a-iii), at a concentration of $1\times10^9$ CFU/AFU dose, and
(a-iv), at a concentration of $1\times10^9$ CFU/AFU dose, and
(a-v), at a concentration of $1\times10^9$ CFU/AFU dose, and
(c-ii), at a concentration of $1\times10^9$ CFU/AFU dose, and
(c-i), tara gum, and, optionally,
(b), preferably maltodextrin.

Advantageously, said second group of vitamins comprises or, alternatively, consists of: (d-i) vitamins of group C, (d-ii) vitamins of group E, (d-iii) vitamins of group B, preferably vitamin B9, and (d-iv) vitamins of group D, preferably vitamin D3; preferably each single vitamin being present at an amount equivalent to 100% RDA (recommended dietary allowance).

Advantageously, said third group of organic and/or inorganic salts comprises or, alternatively, consists of: (e-i) magnesium organic and/or inorganic salts, preferably magnesium glycinate, (e-ii) selenium organic and/or inorganic salts, preferably selenium methionine, and (e-iii) zinc organic and/or inorganic salts, preferably zinc gluconate; preferably each single salt being present at an amount equivalent to 100% RDA.

Advantageously, said third group of organic and/or inorganic salts consists of: (f-i) magnesium glycinate, (f-ii) selenium methionine, and (f-iii) zinc gluconate; preferably each single salt being present at an amount equivalent to 100% RDA.

Advantageously, said fourth group of antioxidant substances comprises or, alternatively, consists of: (f-i) N-acetyl cysteine (NAC), (f-ii) Coenzyme Q10 (CoQ10) and (f-iii) acetyl-L-carnitine (ALC); preferably each single antioxidant substance being present at an amount equivalent to 100 mg/day.

The presence of antioxidant substances in the composition (C) of the invention contributes towards regulating the sleep and mood state of the person to whom said composition (C) is administered. For example, CoQ10 reduces oxidative stress and promotes the correct mitochondrial operation even at the neurons level, with ensuing impact on the regulation of serotonin. Serotonin is a substance that plays a crucial role in the central nervous system and numerous functions including regulating mood state, sleep.

Advantageously, said composition (C) comprises or, alternatively, consists of:
(a) the bacteria strains mixture (M) comprising or, alternatively, consisting of:
(a-i), at a concentration of $1\times10^9$ CFU/AFU dose, and
(a-ii), at a concentration ofi $1\times10^9$ CFU/AFU dose, and/or
(a-iii), at a concentration of $1\times10^9$ CFU/AFU dose, and
(a-iv), at a concentration of $1\times10^9$ CFU/AFU dose, and
(a-v), at a concentration of $1\times10^9$ CFU/AFU dose; and/or
(c) the gum-bacterial strain combination comprising or, alternatively, consisting of:
(c-ii), at a concentration of $1\times10^9$ CFU/AFU dose, and
(c-i), preferably tara gum; and/or
(d) at least one vitamin selected from among the group of vitamins comprising or, alternatively, consisting of:
(d-i), at an amount equivalent to 100% RDA,
(d-ii), at an amount equivalent to 100% RDA,
(d-iii), preferably vitamin B9, at an amount equivalent to 100% RDA, and
(d-iv), preferably vitamin D3, at an amount equivalent to 100% RDA; and/or
(e) at least one salt selected from among the third group of organic and/or inorganic salts comprising or, alternatively, consisting of:
(e-i) magnesium glycinate, at an amount equivalent to 100% RDA,
(e-ii) selenium methionine, at an amount equivalent to 100% RDA, and
(e-iii) zinc gluconate, at an amount equivalent to 100% RDA; and/or
(f) at least one substance selected from among the fourth group of antioxidant substances comprising or, alternatively, consisting of:
(f-i) N-acetyl cysteine (NAC), at an amount equivalent to 100 mg/day,
(f-ii) Coenzyme Q10 (CoQ10), at an amount equivalent to 100 mg/day, and
(f-iii) Acetyl-L-carnitine (ALC), at an amount equivalent to 100 mg/day, and, optionally,
(b), preferably maltodextrin.

Advantageously, the bacterial strains of said bacteria strains mixture (M) and the *S. thermophilus* ST10 DSM 25246 bacteria strain, if optionally present, are present in the composition (C) of the present invention at an amount comprised between 1% and 60% by weight, preferably between 5% and 40% by weight, even more preferably between 10% a 30% by weight, with respect to the total weight of the mixture. However, said percentage depends on the type of pharmaceutical or food form intended to be obtained.

Advantageously, the daily intake of the composition (C) can be comprised between 0.2 g and 10 g.

The bacteria strains of the mixture (M) can be present in the composition (C) in solid form, for example in form of powder, dried powder, or lyophilised powder.

The composition (C) can be in any form suitable for administration to a subject and known to a man skilled in the art such as, by way of non-limiting example, in solid, granular, powder, capsules, tablets, gel, softgel, liquid, slid-liquid suspension and emulsion form.

The composition (C) can be administered to a subject orally or parenterally.

Furthermore, the present invention provides a pharmaceutical preparation or a medical device or a food supplement or a foodstuff comprising the aforementioned composition (C) comprising (a) bacteria strains mixture (M) comprising or, alternatively, consisting of at least one bacteria strain selected from among the group comprising or, alternatively, consisting of: (a-i), (a-ii), (a-iii), (a-iv) and (a-v) as defined above, and,optionally, (b) and/or (c) and/or (d) and/or (e) and/or (f) as defined above, for use in a method for treating and/or improving a sleep disorder, preferably insomnia, and/or a sleep quality disorder or, alternatively, mood modulation disorder or mood dysregulation disorder, in particular mood instability over time, both for healthy subjects (use for non-therapeutic purposes) and for pathological subjects (therapeutic purposes) who has been diagnosed with one of said disorders.

The composition (C) according to the present invention for use in the treatment methods described in the present invention in subjects in need can be administered to said subjects both singularly and as coadjuvants of other compounds, pharmaceutical preparations, medical devices, food supplements or foodstuffs effective in the treatment of the diseases or disorders or symptoms.

The composition (C) according to the present invention can be for use in the treatment methods described in the present invention in human subjects or for veterinarian use, by way of non-limiting example, in pets such as dogs or cats, or in other mammals. Preferably, the composition according to the present invention is for use in humans.

Lastly, the present invention provides a method for treating subjects suffering from a sleep disorder, preferably insomnia and/or a sleep quality disorder or, alternatively, a mood dysregulation, in particular suffering from a mood instability over time, wherein said treatment method provides for administration of said composition (C) of the invention as defined above, to said subjects.

Advantageously, the taking of the composition (C) comprising the bacteria strains mixture (M) of the present invention reveals considerable changes in subjects after taking the same (effectiveness). In particular, continuous taking of the composition (C) improves the sleep quality perceived in the treated persons (pathological or healthy persons).

Furthermore, the continuous taking of the composition (C) modulates sleep stabilising it over time at a state inclined towards optimism capable of overcoming the sadness and pessimism states (e.g. positive attitude in the presence of challenging/stressing situations, adopting a more optimal behaviour overcoming states of sadness, cognitive reactivity to moderate sadness emotional states, adopting a personality open towards novelty, persistent and cooperative) in the treated people (pathological or healthy persons). Furthermore, the continuous taking of the composition (C) does not reveal adverse effects.

Experimental Part

The Applicant conducted an in vivo study during which the Applicant carried out an evaluation of the probiotics administration effects in healthy subjects in terms of improvement of sleep quality and psychological conditions, in particular the mood state, through some markers such as inclination towards optimism and cognitive reactivity.

1. Methods and Materials 1.1 Stud Population

A double-blind randomised study (experimenter and participants) of the case-control type.

The sample in question consists of two groups of healthy subjects aged between 18 and 35 years:
Experimental group (G1): the subjects of this group (19 participants) took the composition subject of the present invention (Composition C, see point 2) for six weeks.

Control group (G2): the subjects of this group (19 participants) took a placebo for six weeks. In particular, a total of 33 people completed the study. Out of this total group, 18 participants took part in the experimental group treated with a composition (C) comprising probiotics (11 men and 7 women, mean age: 21.61±2.20) and 15 participants took part in the untreated control group (10 men and 5 women, mean age: 21.65±2.16). The subjects taking part in the study were not subjected to a continuous pharmacological treatment or recent treatment using antibiotics and without diseases such as gastrointestinal disorders, food intolerances, allergies, chronic diseases.

1.2 Administered Composition C or Placebo

Administered in the experimental group (G1) was a composition C in granular form for oral solution (3.0 grams/sachet) comprising a probiotics strains mixture M with a concentration of $4 \times 10^9$ CFU/AFU sachet-daily intake (CFU: Colony Forming Units; AFU: Active Fluorescent Units).

The composition (C) comprises a bacterial strains mixture (M) of the following lyophilised probiotic strains:

0.1 g of a *Lactobacillus fermentum* LF16 DSM 26956 bacterium strain, at a concentration of $1 \times 10^9$ CFU/AFU; and 0.1 g of a *Lactobacillus plantarum* LP01 LMG P-21021 bacterium strain, at a concentration of $1 \times 10^9$ CFU/AFU; and 0.1 g of a *Lactobacillus rhamnosus* LR06 DSM 21981 bacterium strain, at a concentration of $1 \times 10^9$ CFU/AFU; and 0.1 g of a *Bifidobacterium longum* BL04 DSM 23233 bacterium strain is present at a concentration of $1 \times 10^9$ CFU/AFU, and 2,6 g of maltodextrin, added to probiotic strains as loading agents to obtain the composition.

Also tested was a composition C in granular form for oral solution (2.5 grams/sachet) comprising a probiotic strains mixture M with a concentration of $4 \times 10^9$ CFU/AFU sachet-daily intake (CFU: Colony Forming Units; AFU: Active Fluorescent Units).

The composition (C) comprises a bacterial strains mixture (M) of the following lyophilised probiotic strains:

0.1 g of a *Lactobacillus fermentum* LF16 DSM 26956 bacterium strain, at a concentration of $1 \times 10^9$ CFU/AFU; and 0.1 g of a *Lactobacillus plantarum* LP01 LMG P-21021 bacterium strain, at a concentration of $1 \times 10^9$ CFU/AFU; and 0.1 g of a *Lactobacillus rhamnosus* LR06 DSM 21981 bacterium strain, at a concentration of $1 \times 10^9$ CFU/AFU; and 0.1 g of a *Bifidobacterium longum* BL04 DSM 23233 bacterium strain is present at a concentration of $1 \times 10^9$ CFU/AFU, and 2.1 g of maltodextrin, added to probiotic strains as loading agents to obtain the composition.

Administered in the control group (G2) was the placebo containing maltodextrin (2.5 g, daily intake) as a single component of the granulate for oral solution.

1.3 Study Design

The experimental trial lasted 9 weeks divided into evaluation sessions (T0, T1, T2, T3—see diagram, FIG. 1). During each evaluation session, the students filled out the evaluation/psychological questionnaires (see the description of the questionnaires at point 2.) and submitted the stools samples. The daily taking of the probiotic or of the placebo product commenced starting from the day following the day of first evaluation (T0) and it lasted for 6 weeks (up to the session T2), with an intermediate evaluation at three weeks from the date when the product commenced being taken (T1) (FIG. 1). Upon completing the six weeks of the taking of the product (probiotic or placebo), the students ceased taking any product for another three weeks and they filled out the evaluation T4 at the end of said 3 weeks (FIG. 1).

1.4 Data Statistical Analysis

Software for questionnaire analysis at times T0, T1, T2, T3→SPSS Statistics 19 (IBM Corp., NY, USA).

Confidence interval 95%, significance level $p<0.05$.

Comparison between groups in each session (Experimental vs. Control)→Mann-Whitney U test.

Comparison between sessions in each group→Friedman test.

Post-hoc comparisons: Wilcoxon Signed Rank test (Bonferroni corrected $p<0.012$).

2. Evaluation Questionnaires and Related Results

Described below are the results for each cognitive test.

Graphically shown in FIGS. 2-8 are said results with the significance levels indicated by an asterisk if referring to the existing statistically significant difference between groups or by an asterisk and a strikethrough if referring to the existing statistically significant difference between the various Sessions for each group. Indicated on the ordinates axis is the questionnaire mean score as regards the Experimental group (treated with probiotic mixture—G1, light grey) and the Control group (treated with placebo—G2, dark grey).

Numerically indicated in Tables 1-3 are the results illustrated in FIGS. 2-8, with standard deviation shown between brackets.

2.1 Pittsburgh Sleep Quality Index (PSQI, Buysse et al., 1989; Curcio et al., 2013) (FIG. 2)

Evaluation of the sleep quality perceived by the subject.

Score in inverse relationship with respect to the parameter subject of the study: the lower the assigned score, the higher the perceived sleep quality.

The score difference between the sessions T2 and T0 ($p=0.005$) with maintenance at T3, (T0-T3 $p=0.017$) (Bonferroni correction for $p<0.012$) is significant in the Experimental group (G1).

2.2 Cope Orientation to Problem Experienced (COPE-NVI, Sica C. et al., 2008) (FIGS. 3A, 3B, 3C, 3D and 3E)

Evaluation of the response of the persons faced with stressing events or situations; five subscales: Social support, Avoidance strategies, Positive attitude, Orientation to problem, Orientation to transcendence.

The higher the subscale total score, the greater the frequency when adopting a positive strategy when addressing the description subject of such subscale.

Avoidance strategies subscale, between the two groups G1 and G2 significant effect at times T2 ($p=0.010$) and T3 ($p=0.006$).

Positive attitude subscale, between the two groups G1 and G2 significant effect at time T1 ($p=0.016$).

2.3 Index of Depression Sensitivity-Revised test (LEIDS-R, van der Does W. et al., 2003) (FIGS. 4A, 4B, 4C, 4D, 4E and 4F)

Evaluation of cognitive reactivity towards mild sadness emotional states; six subscales: Hopelessness, Acceptance, Aggressiveness, Rumination, Risk control and Aversion.

The higher the subscale score, the greater the vulnerability with respect to the magnitude subject of evaluation.

Acceptance subscale, significant difference between the Experimental group (G1) with respect to the Control group (G2) at T2 ($p=0.031$).

2.4 Temperament and Character Inventory test (TCI, Cloninger CR. et al., 1994)) (FIGS. 5A, 5B, 5C, 5D, 5E, 5F and 5G)

Evaluation of personal differences based on the character; seven subscales: Novelty-seeking, Avoiding damage, Reward dependence, Persistence, Self-direction, Cooperativeness, Self-transcendence.

The higher the total score, the higher the level of the magnitude of the character described by the scale.

Novelty-seeking subscale, significant difference between the Experimental group (G1) with respect to a Control group (G2) at T3 (p=0.027).

Persistence subscale, significant difference between the Experimental group (G1) with respect to the Control group (G2) all 4 times (T0, p=0.002; T1 p=0.004; T2, p=0.003; T3 p=0.005.

Self-direction subscale, significant difference between the Experimental group (G1) with respect to the Control group (G2) at T3 (p=0.013).

Cooperativeness subscale, significant difference between the Experimental group (G1) with respect to the Control group (G2) at T2 (p=0.023-0.026).

2.5 Behavioural Inhibition and Behavioural Activation Scale (BIS-BAS, Leone L. et al., 1994) (FIGS. 6A, 6B, 6C and 6D)

Evaluation of the dispositional sensitivity towards the behavioural inhibition system (BIS).

Evaluation of the dispositional sensitivity towards behavioural approach or activation system (BAS); three subscales: BAS-Guide, BAS-Fun-seeking, BAS-Reward Reactivity.

No significant data; this denotes a non-activity of the probiotic mixture on tendency towards the action correlated to high impulsivity levels (BIS) and on the avoidance tendency correlated to high anxiety levels (BAS).

2.6 Life-Orientation Test-Revisited (LOT-R, Scheier et al., 1994) (FIG. 7)

Evaluation of predisposition towards pessimism and optimism.

The higher the total score, the higher the degree of optimism (high optimism, 19-24, moderate optimism, 14-18, low optimism, 0-13).

In the Experimental group, effect tending towards significant between T2 and T0 (p=0.014) and between T3 and T0 (p=0.003) due to an increase of the optimism scores.

2.7 Profile of mood state (POMS, McNair et al., 1964) (FIGS. 8A, 8B, 8C, 8D, 8E and 8F)

Evaluation of mood states; six subscales: Tension-Anxiety, Depression-Dejection, Aggressiveness-Anger, Vigour-Activity, Tiredness-Indolence and Confusion-Disconcert.

The higher the total score of the scale, the higher the level of the correlated mood.

Depression-Dejection subscale, significant effect in the Experimental group between T2 and T0 (p=0.009), tendency towards significance at T3(p=0.014) with respect to T0.

Aggressiveness-Anger subscale, significant effect in the Experimental group between T1 and T0 (p=0.007), tendency towards significance at T2 (p=0.016) as well as at T3 (p=0.003) with respect to T0.

Tiredness-Indolence subscale (p=0.008), significant effect in the Experimental group between T2 and T0 (p=0.005) and between T3 and T0 (p=0.011).

3. Results

This object of this study was to investigate the effect of taking the composition of the present invention comprising probiotics (Composition C) on some aspects related to the mood, cognitive functions and sleep perception. In particular, the difference between the experimental group (G1, administration of probiotics) and the control group (G2, administration of placebo) in the aforementioned aspects was evaluated through special questionnaires. The results show that taking the composition (C) continuously improves the perceived sleep quality (PSQI test) and stabilises mood over time at a state leaning towards optimism capable of overcoming sadness and pessimism states. As a matter of fact, as concerns the evaluation of the effect obtained from taking probiotics on mood, there was observed a positive impact of the composition (C) in adopting a positive attitude when faced with challenging/stressing situations (COPE test), in adopting a more optimist behaviour overcoming sadness states (LOT-R test), in cognitive reactivity towards mild sadness emotional states (LEIDS-R test), in adopting a character open towards novelty, persistent and cooperative (TCI test) and in the considerable reduction of anxiety state and in the considerable improvement of the general emotional state of the subjects (reduction of dejection/depression, reduction of aggressiveness/anger, reduction of tiredness/indolence and reduction of stress-related confusion states; POMS test). Furthermore, the absence of significant effects in the BIS-BAS tests revealed a non-activity of the composition (C) to facilitate a tendency towards the action correlated to high impulsivity levels (BIS) and a tendency towards the action correlated to high anxiety levels (BAS).

No adverse effect was observed in the experimental group (G1).

TABLE 1

| | Experimental Group (G1) | | | | Control Group (G2) | | | |
| | Sessions | | | | Sessions | | | |
| | T0 | T1 | T2 | T3 | T0 | T1 | T2 | T3 |
| PSQI | 5.61 | 4.67 | 4.00 | 4.22 | 4.67 | 3.87 | 4.33 | 4.13 |
| | (2.17) | (2.35) | (1.64) | (1.86) | (2.61) | (2.59) | (2.66) | (2.70) |

TABLE 2

|  | Experimental Group (G1) | | | | Control Group (G2) | | | |
|  | Sessions | | | | Sessions | | | |
|  | T0 | T1 | T2 | T3 | T0 | T1 | T2 | T3 |
| --- | --- | --- | --- | --- | --- | --- | --- | --- |
| LEIDS-R | | | | | | | | |
| Hopelessness | 5.44 (5.16) | 5.06 (5.82) | 5.00 (4.68) | 6.11 (5.55) | 3.33 (3.35) | 3.40 (3.22) | 2.93 (3.71) | 3.33 (3.09) |
| Acceptance | 4.78 (3.47) | 4.22 (4.41) | 5.33 (5.11) | 5.83 (4.94) | 2.80 (3.49) | 3.33 (3.20) | 2.93 (3.51) | 2.93 (2.49) |
| Aggressiveness | 8.39 (4.55) | 9.00 (4.96) | 8.22 (4.66) | 8.94 (5.24) | 7.53 (3.70) | 5.93 (3.53) | 5.20 (2.57) | 5.47 (4.32) |
| Control | 7.72 (3.12) | 7.61 (5.23) | 7.72 (3.88) | 8.06 (3.28) | 7.07 (4.38) | 6.87 (4.81) | 6.73 (4.18) | 6.80 (4.14) |
| Risk aversion | 10.22 (3.10) | 9.39 (3.94) | 9.78 (3.59) | 10.33 (3.82) | 9.00 (2.75) | 9.27 (3.61) | 8.53 (6.64) | 7.87 (4.26) |
| Rumination | 11.61 (3.85) | 10 (5.20) | 11.17 (4.63) | 10.06 (4.19) | 12.20 (5.88) | 10.53 (6.27) | 9.93 (4.77) | 10.33 (5.65) |
| POMS | | | | | | | | |
| Tension | 8.61 (5.34) | 6.00 (4.07) | 5.89 (3.56) | 5.44 (5.59) | 12.40 (6.73) | 8.47 (5.89) | 9.40 (6.24) | 8.47 (5.94) |
| Depression | 11.00 (9.45) | 7.28 (8.80) | 6.22 (7.26) | 5.67 (7.15) | 9.80 (9.64) | 11.80 (12.34) | 8.53 (9.33) | 8.73 (9.18) |
| Anger | 10.39 (6.79) | 6.56 (4.87) | 6.78 (5.11) | 5.28 (4.66) | 11.40 (9.21) | 9.13 (10.24) | 9.60 (6.98) | 8.53 (9.49) |
| Vigour | 16.78 (3.89) | 18.06 (4.84) | 16.17 (5.70) | 17.61 (6.25) | 15.40 (7.39) | 17.00 (7.19) | 15.00 (7.31) | 14.87 (8.10) |
| Fatigue | 8.89 (4.30) | 7.06 (4.24) | 5.28 (3.97) | 5.33 (4.12) | 10.53 (5.01) | 8.40 (5.18) | 7.87 (4.58) | 7.20 (5.45) |
| Confusion | 9.50 (3.47) | 8.78 (4.02) | 7.33 (4.83) | 6.89 (5.14) | 10.33 (5.96) | 11.13 (6.17) | 10.13 (6.64) | 7.80 (3.97) |

TABLE 3

|  | Experimental group (G1) | | | | Control Group (G2) | | | |
|  | Sessions | | | | Sessions | | | |
|  | T0 | T1 | T2 | T3 | T0 | T1 | T2 | T3 |
| --- | --- | --- | --- | --- | --- | --- | --- | --- |
| TCI | | | | | | | | |
| Novelty-seeking | 21.39 (4.33) | 22.50 (5.14) | 22.44 (5.39) | 22.22 (5.80) | 17.47 (5.10) | 18.80 (6.22) | 18.53 (7.06) | 17.60 (4.95) |
| Avoiding damage | 14.39 (5.94) | 14.94 (7.57) | 13.61 (7.40) | 12.72 (7.27) | 16.27 (6.47) | 14.73 (8.28) | 14.20 (8.16) | 14.33 (8.93) |
| Reward dependence | 13.83 (4.41) | 14.39 (4.65) | 13.61 (4.41) | 13.11 (3.89) | 15.47 (4.47) | 16.00 (4.60) | 15.53 (3.93) | 15.13 (4.45) |
| Persistence | 4.00 (1.94) | 3.94 (1.95) | 3.72 (1.71) | 4.17 (1.76) | 5.93 (1.10) | 5.93 (1.44) | 5.73 (1.67) | 6.00 (1.65) |
| Self-direction | 25.89 (7.51) | 24.44 (6.78) | 24.94 (7.25) | 23.61 (8.41) | 29.00 (7.13) | 28.73 (8.58) | 30.60 (7.95) | 31.33 (7.35) |
| Cooperativeness | 29.39 (7.54) | 29.78 (6.90) | 29.83 (6.25) | 30.39 (7.07) | 33.00 (5.13) | 33.67 (5.14) | 34.20 (4.23) | 34.13 (4.41) |
| Self-transcendence | 12.11 (4.44) | 13.28 (5.29) | 10.72 (5.28) | 11.89 (5.72) | 13.60 (6.62) | 14.60 (7.57) | 13.87 (7.89) | 13.00 (8.26) |
| COPE | | | | | | | | |
| Social support | 30.33 (6.99) | 30.28 (8.92) | 30.67 (7.86) | 30.94 (9.08) | 32.07 (11.30) | 33.87 (10.69) | 31.47 (10.39) | 32.00 (10.51) |
| Avoidance strategies | 29.00 (6.02) | 28.61 (7.22) | 28.72 (7.60) | 29.06 (7.06) | 22.47 (3.83) | 24.13 (4.90) | 22.73 (4.70) | 22.87 (5.01) |
| Positive attitude | 32.94 (3.39) | 30.78 (4.18) | 32.11 (5.04) | 31.89 (3.27) | 36.33 (4.62) | 35.53 (6.06) | 34.67 (5.16) | 34.00 (5.24) |
| Orientation to problem | 31.06 (4.49) | 30.94 (4.71) | 31.28 (6.44) | 30.39 (6.14) | 35.20 (4.69) | 33.00 (6.36) | 32.07 (7.07) | 31.73 (6.35) |
| Orientation to transcendence | 16.50 (3.73) | 16.11 (3.50) | 16.22 (4.25) | 15.72 (3.34) | 18.20 (5.56) | 18.13 (5.03) | 17.93 (5.54) | 17.47 (5.53) |

TABLE 3-continued

| | Experimental group (G1) | | | | Control Group (G2) | | | |
| | Sessions | | | | Sessions | | | |
| | T0 | T1 | T2 | T3 | T0 | T1 | T2 | T3 |
|---|---|---|---|---|---|---|---|---|
| BIS/BAS | | | | | | | | |
| BIS | 20.83 | 19.89 | 20.00 | 20.89 | 21.20 | 21.73 | 20.53 | 21.00 |
| | (3.22) | (3.77) | (3.61) | (3.27) | (3.55) | (3.39) | (2.88) | (2.56) |
| BAS - Guide | 13.22 | 13.83 | 13.72 | 14.00 | 13.07 | 13.27 | 12.93 | 13.60 |
| | (3.19) | (3.15) | (2.82) | (2.57) | (2.96) | (2.31) | (2.74) | (2.92) |
| BAS - Fun-seeking | 13.83 | 13.67 | 14.28 | 14.06 | 12.60 | 12.53 | 13.13 | 13.27 |
| | (3.29) | (3.24) | (3.21) | (3.06) | (3.46) | (3.91) | (4.05) | (3.51) |
| BAS- Reward reactivity | 20.94 | 20.61 | 20.83 | 20.94 | 21.27 | 21.40 | 20.93 | 21.33 |
| | (2.82) | (2.95) | (3.40) | (2.84) | (3.20) | (2.95) | (2.99) | (3.44) |
| LOT-r | 14.06 | 14.72 | 16.17 | 16.44 | 15.47 | 16.27 | 15.40 | 16.13 |
| | (4.65) | (5.10) | (3.67) | (4.36) | (4.07) | (5.31) | (3.87) | (5.22) |

The invention claimed is:

1. A method for modulating the mood of a subject, comprising administering to the subject a therapeutically effective amount of a composition (C) comprising:
   (a) a bacteria strains mixture (M) comprising or consisting of:
   (a-i) a bacterium strain of the *Lactobacillus fermentum* species identified as the *Lactobacillus fermentum* LF16 DSM 26956 bacterium strain,
   (a-ii) a bacterium strain of the *Lactobacillus plantarum* species identified as the *Lactobacillus plantarum* LP01 LMG P-21021 bacterium strain, and/or a bacterium strain of the *Lactobacillus plantarum* species identified as the *Lactobacillus plantarum* LP02 LMG P-21020 bacterium strain,
   (a-iii) a bacterium strain of the *Lactobacillus rhamnosus* species identified as the *Lactobacillus rhamnosus* LR06 DSM 21981 bacterium strain; and
   (a-iv) a bacterium strain of the *Bifidobacterium longum* species identified as the *Bifidobacterium longum* BL04 DSM 23233 bacterium strain;
   and, optionally,
   (b) at least one technological additive and/or at least one pharmaceutical or food grade excipient, to facilitate mood modulation in a subject.

2. The method of claim 1, wherein said (a) bacteria strains mixture (M) comprises
   each strain at a concentration comprised between $1 \times 10^8$ CFU (Colony forming units) and $1 \times 10^{12}$ CFU(Colony forming units), with respect to the daily intake.

3. The method of claim 1, wherein said composition (C) further comprises:
   (c) at least one natural vegetable gum and/or *S. thermophilus* bacteria strain ST10 DSM 25246; and/or
   (d) at least one vitamin selected from a second group of vitamins consisting of: (d-i) vitamins of group C, (d-ii) vitamins of group E, (d-iii) vitamins of group B and (c-iv) vitamins of group D; and/or
   (e) at least one salt selected from a third group of organic and/or inorganic salts consisting of: (e-i) magnesium organic and/or inorganic salts, (e-ii) selenium organic and/or inorganic salts, (e-iii) zinc organic and/or inorganic salts; wherein said magnesium salt (e-i) is magnesium glycinate, said selenium salt (e-ii) is selenium methionine and said zinc salt (e-iii) is zinc gluconate; and/or
   (f) at least one substance selected from a fourth group of antioxidant substances consisting of: (f-i)N-acetyl cysteine (NAC), (f-ii) Coenzyme Q10 (CoQ10) and (f-iii) acetyl-L-carnitine (ALC).

* * * * *